United States Patent
Juzkiw et al.

(10) Patent No.: US 9,168,085 B2
(45) Date of Patent: Oct. 27, 2015

(54) MONITORING AND CONTROLLING ENERGY DELIVERY OF AN ELECTROSURGICAL DEVICE

(75) Inventors: Taras Juzkiw, Mississauga (CA); Jonathan Dandy, Beaverton, OR (US)

(73) Assignee: BAYLIS MEDICAL COMPANY INC., Montreal, Quebec (CA)

(*) Notice: Subject to any disclaimer, the term of this patent is extended or adjusted under 35 U.S.C. 154(b) by 689 days.

(21) Appl. No.: 13/410,868

(22) Filed: Mar. 2, 2012

(65) Prior Publication Data

US 2012/0215213 A1 Aug. 23, 2012

Related U.S. Application Data

(63) Continuation-in-part of application No. 13/286,041, filed on Oct. 31, 2011, now Pat. No. 8,623,005, which is a continuation-in-part of application No. 11/905,448, filed on Oct. 1, 2007, now Pat. No. 8,048,071.

(Continued)

(51) Int. Cl.
*A61B 18/18* (2006.01)
*A61B 18/14* (2006.01)
(Continued)

(52) U.S. Cl.
CPC . *A61B 18/14* (2013.01); *A61B 8/12* (2013.01); *A61B 18/1233* (2013.01); *A61B 18/16* (2013.01);
(Continued)

(58) Field of Classification Search
CPC ............... A61B 2018/00083; A61B 18/1492; A61B 18/18; A61B 2018/00214; A61B 2018/00702; A61B 2018/00827; A61B 2018/00875; A61B 2018/00898; A61B 8/12; A61B 18/1233; A61B 18/14; A61B 18/16; A61B 19/24; A61B 2017/00119; A61B 2017/00132
USPC ....................................................... 606/32–45
See application file for complete search history.

(56) References Cited

U.S. PATENT DOCUMENTS 5,300,068 A * 4/1994 Rosar et al. ..................... 606/34
5,372,596 A * 12/1994 Klicek et al. .................... 606/35
(Continued)

FOREIGN PATENT DOCUMENTS

| AU | WO2007082343 A1 | 7/2007 |
| EP | 1920724 A1 | 5/2008 |

(Continued)

OTHER PUBLICATIONS

Frank R. Arko III, "In Pursuit of an Off-the-Shelf Fenestrated Stent-Graft: Radiofrequency Perforation for In Vivo Anteagrade Fenestration","Journal of Endovascular Therapy", Apr. 2010, pp. 199-200, vol. 17, No. 2, Publisher: Journal of Endovascular Therapy, Published in: US.

(Continued)

*Primary Examiner* — Joseph Stoklosa
*Assistant Examiner* — Amanda Zink
(74) *Attorney, Agent, or Firm* — Nir Lifshitz; Glenn Arnold

(57) ABSTRACT

A method is disclosed for delivering energy to a region of tissue within a patient's body using a medical treatment system. The medical treatment system comprises an energy delivery device coupled to an energy source. Energy is delivered through the energy delivery device positioned within the patient's body. An energy delivery parameter associated with the delivery of energy by the medical treatment system is monitored and if one or more values of the energy delivery parameter exceed a predetermined magnitude threshold, one or more errors are detected. The extent of the detected errors is determined or assessed and the delivery of energy is controlled if the extent of the errors detected exceeds a sensitivity threshold before the expiry of a predetermined time period.

6 Claims, 8 Drawing Sheets

Related U.S. Application Data

(60) Provisional application No. 60/827,466, filed on Sep. 29, 2006, provisional application No. 61/448,578, filed on Mar. 2, 2011.

(51) Int. Cl.
| | | |
|---|---|---|
| *A61B 8/12* | (2006.01) | |
| *A61B 17/00* | (2006.01) | |
| *A61B 18/00* | (2006.01) | |
| *A61B 18/12* | (2006.01) | |
| *A61B 18/16* | (2006.01) | |

(52) U.S. Cl.
CPC ............... *A61B 2017/00119* (2013.01); *A61B 2018/0072* (2013.01); *A61B 2018/00083* (2013.01); *A61B 2018/00214* (2013.01); *A61B 2018/00601* (2013.01); *A61B 2018/00678* (2013.01); *A61B 2018/00702* (2013.01); *A61B 2018/00827* (2013.01); *A61B 2018/00875* (2013.01); *A61B 2018/00898* (2013.01); *A61B 2018/1213* (2013.01); *A61B 2018/141* (2013.01)

(56) References Cited

U.S. PATENT DOCUMENTS

| | | | |
|---|---|---|---|
| 5,540,681 A * | 7/1996 | Strul et al. | 606/34 |
| 5,617,878 A | 4/1997 | Taheri | |
| 5,720,744 A * | 2/1998 | Eggleston et al. | 606/40 |
| 6,142,992 A | 11/2000 | Cheng et al. | |
| 6,296,636 B1 | 10/2001 | Cheng et al. | |
| 6,364,877 B1 | 4/2002 | Goble et al. | |
| 7,651,492 B2 | 1/2010 | Wham | |
| 2002/0022836 A1 | 2/2002 | Goble et al. | |
| 2004/0030328 A1* | 2/2004 | Eggers et al. | 606/34 |
| 2005/0085806 A1* | 4/2005 | Auge et al. | 606/32 |
| 2005/0149012 A1* | 7/2005 | Penny et al. | 606/41 |
| 2005/0203504 A1* | 9/2005 | Wham et al. | 606/34 |
| 2006/0106375 A1* | 5/2006 | Werneth et al. | 606/32 |
| 2007/0118099 A1 | 5/2007 | Trout, III | |
| 2007/0208256 A1 | 9/2007 | Marilla | |
| 2008/0108987 A1 | 5/2008 | Bruszewski et al. | |
| 2009/0264977 A1 | 10/2009 | Bruszewski et al. | |
| 2010/0125282 A1 | 5/2010 | Machek et al. | |
| 2010/0179632 A1 | 7/2010 | Bruszewski et al. | |

FOREIGN PATENT DOCUMENTS

| | | |
|---|---|---|
| EP | 1943974 A1 | 7/2008 |
| GB | 2437058 | 10/2007 |

OTHER PUBLICATIONS

Leonard W. H. Tse et al., "Rediofrequency Perforation Systen for In Vivo Antegrade Fenestration of Aortic Stent-Grafts","Journal of Endovascular Therapy", Apr. 2010, pp. 192-198, vol. 17, No. 2, Publisher: Journal of Endovascular Therapy, Published in: US.

John Lennon Anderson et al., "Endoluminal Aortic Grafting with Renal and Superior Mesentric Artery Incorporation by Graft Fenestration", "Journal of Endovascular Therapy", Feb. 2001, pp. 3-15, No. 8, Publisher: Journal of Endovascular Therapy, Published in: US.

Abstract of Leonard W.H. Tse et al., "In Vivo Antegrade Fenestration of Abdominal Aortic Stent-Grafts", "Journal of Endovascular Therapy", Apr. 2007, pp. 158-167, vol. 14, No. 2, Publisher: Journal of Endovascular Therapy, Published in: US.

Timothy A.M. Chuter, "Branched and Fenestrated Stent Grafts for Endovascular Repair of Thoracic Aortic Aneurysms", Oct. 27, 20085, pp. 111A-115A, vol. 43, No. A, Publisher: The Society for Vascular Surgery, Published in: US.

Abstract of Richard G. McWilliams et al., "In Situ Stent-Graft Fenestration to Preserve the Left Subclavian Artery", "Journal of Endovascular Therapy", Apr. 2004, pp. 170-174, vol. 11, No. 2, Publisher: Journal of Endovascular Therapy, Published in: US.

Brendan M. Stanley et al., "Fenestration in Endovascular Grafts for Aortic Aneurysm Repair: New Horizons for Preserving Blood Flow in Branch Vessels", "Journal of Endovascular Therapy", Feb. 2001, pp. 16-24, vol. 8, Publisher: Journal of Endovascular Therapy, Published in: US.

Edward B. Diethrich, "Side Branch Preservation During Endovascular Aortic Aneurysm Repair", "Journal of Endovascular Therapy", Feb. 2001, pp. 1-2, vol. 8, Publisher: Journal of Endovascular Therapy, Published in: US.

Abstract of Richard G. McWilliams et al., "Retrogade Fenestration of Endoluminal Grafts From Target Vessels: Feasibility, Technique, and Potential Usage", "Journal of Endovascular Therapy", Oct. 2003, pp. 946-952, vol. 10, No. 5, Publisher: Journal of Endovascular Therapy, Published in: US.

Entire prosecution history of U.S. Appl. No. 11/905,448 from Oct. 1, 2007 to Aug. 22, 2012; Inventor: Biadillah, Youssef et al.

Entire prosecution history of U.S. Appl. No. 13/286,041 from Oct. 31, 2011 to Aug. 14, 2013; Inventor: Biadillah, Youssef et al.

* cited by examiner

MONITORING AND CONTROLLING ENERGY DELIVERY OF AN ELECTROSURGICAL DEVICE

CROSS-REFERENCES TO RELATED APPLICATIONS

This application is a continuation-in-part of U.S. application Ser. No. 13/286,041, filed on Oct. 31, 2011 which is a continuation-in-part of U.S. patent application Ser. No. 11/905,448, filed on Oct. 1, 2007, which claims the benefit of U.S. provisional patent application No. 60/827,466 filed on 29 Sep. 2006.

This application further claims the benefit of U.S. provisional application No. 61/448,578, filed on Mar. 2, 2011. All of these US patent applications and provisional patent applications are hereby incorporated by reference in their entirety.

TECHNICAL FIELD

The disclosure relates to systems and methods for monitoring and controlling energy delivery of an electrosurgical device. More specifically, the disclosure relates to systems and methods for monitoring and controlling delivery of energy to a region of tissue within a patient's body using an electrosurgical device.

BACKGROUND OF THE ART

U.S. Pat. No. 7,651,492 granted to Wham discloses a system and method for performing electrosurgical procedures. The system includes sensor circuitry adapted to measure impedance and to obtain one or more measured impedance signals. The sensor circuitry is further adapted to generate one or more arc detection signals upon detecting an arcing condition. This is accomplished by passing the measured impedance tissue signal through a high pass filter and then passing the absolute value of the high pass filter through a low pass filter. The resulting filtered signal is the arc detection signal that is scaled and capped. The system disclosed by Wham further includes a controller adapted to generate one or more target control signals as a function of the measured impedance signals and to adjust the output of the electrosurgical generator based on the arc detection signal. Wham discloses detecting arcing by monitoring for rapidly repeating changes in measured signal such as the impedance signal and generating an arc detection signal. Since the system as disclosed by Wham relies on measuring changes in the impedance signal, it will result in the detection of an arcing condition and controlling of the output even if the arcing is insignificant. Furthermore, the system may not respond even if the arcing is significant as long as repeated arcing is not observed. Thus, Wham's system includes several deficiencies with respect to arc detection and energy control.

SUMMARY OF THE DISCLOSURE

In accordance with an embodiment of the present invention, a method is disclosed for delivering energy within a region of tissue within a patient's body. The method helps avoid significant arcing while still allowing use of an energy delivery device in the vicinity of an electrically conductive object such as a metallic object. An energy delivery parameter is monitored during the delivery of energy. The value of the energy delivery parameter is compared to a predetermined magnitude threshold to determine if the value exceeds or falls below the predetermined threshold to ascertain if there is significant arcing. The energy delivery is then controlled based on the extent of the arcing observed.

In one broad aspect, embodiments of the present invention comprise a method and medical treatment system for delivering energy to a region of tissue within a patient's body. The medical treatment system comprises an energy delivery device coupled to an energy source. In one particular embodiment, the method comprises the steps of: delivering energy through said energy delivery device; monitoring a current output of said energy delivery device; detecting one or more over-currents if the current output exceeds a predetermined magnitude threshold; determining an extent of the over-currents detected over a predetermined time period; and controlling the delivery of energy based on the extent of the over-currents detected.

In another broad aspect, embodiments of the present invention comprise a method and medical treatment system for delivering energy to a region of tissue within a patient's body. The medical treatment system comprises an energy delivery device coupled to an energy source. In one particular embodiment, the method comprises the steps of: delivering energy through said energy delivery device (which may be positioned within the patient's body); monitoring an energy delivery parameter (for example an electrical parameter) associated with the delivery of energy by the medical treatment system; detecting one or more errors if one or more values of the energy delivery parameter exceed a predetermined magnitude threshold; determining or assessing an extent of the errors detected; and controlling the delivery of energy if the extent of the errors detected exceeds a sensitivity threshold over a predetermined time period.

As a feature of this broad aspect, the step of determining the extent of the errors comprises a step of determining the number of errors detected.

As another feature of this broad aspect, the step of determining the extent of the errors comprises a step of determining the magnitude of the one or more values of the energy delivery parameter that exceed the predetermined threshold.

As another feature of this broad aspect, the step of determining the extent of the errors comprises a step of determining the duration of time during which the one or more errors are detected.

As another feature of this broad aspect, the energy delivery parameter is selected from the group consisting of: current, voltage, impedance and power.

As a feature of this broad aspect, the energy delivery device is an RF (radiofrequency) cutting device.

As an alternate feature of this broad aspect, the energy delivery device is an RF (radiofrequency) ablation device.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
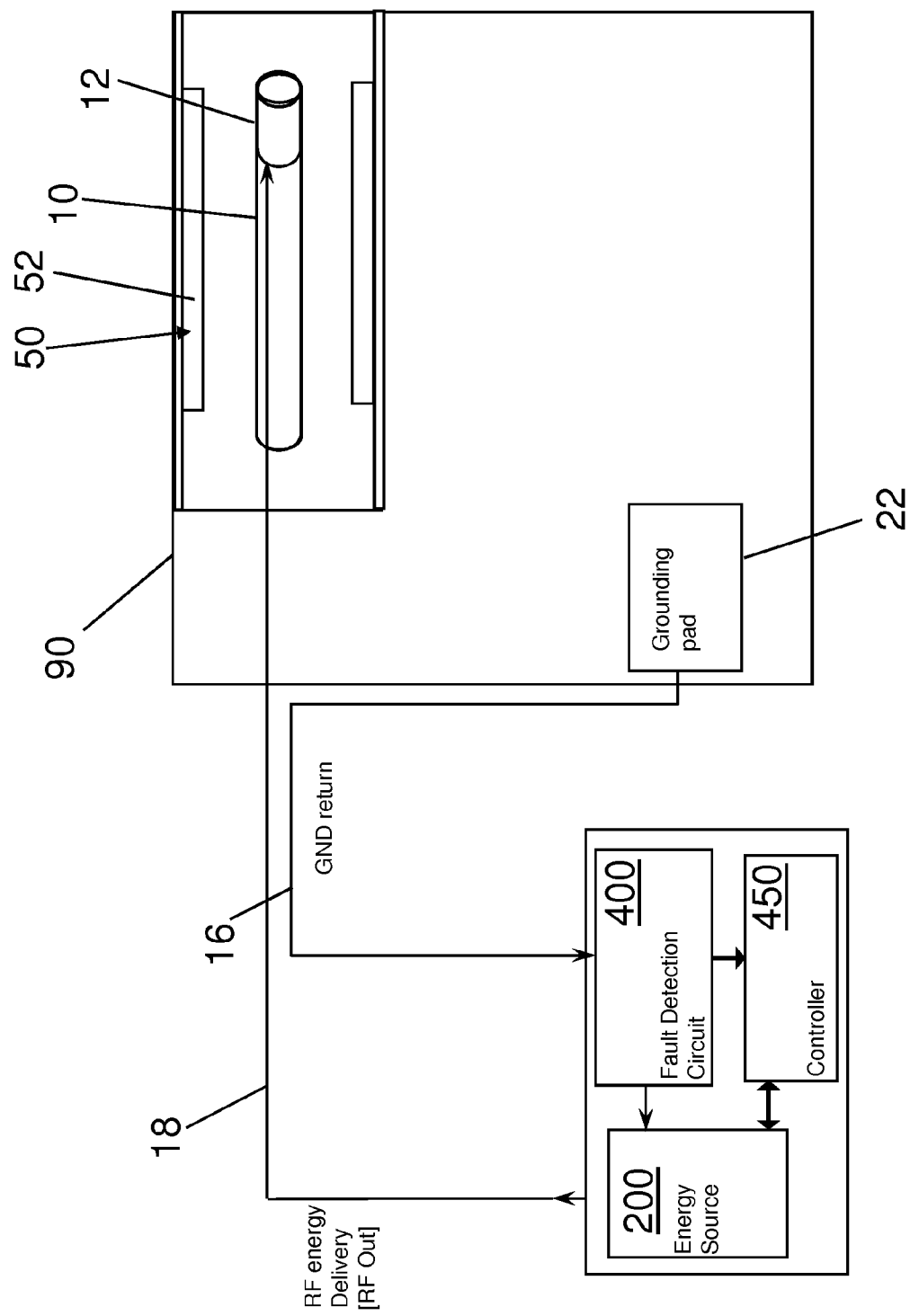
FIG. 1a is an illustration of a medical treatment system in accordance with an embodiment of the present invention.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In accordance with an embodiment of the present invention a method is disclosed for delivering energy within a region of tissue within a patient's body. The method helps avoid significant arcing while allowing use of an energy delivery device in the vicinity of an electrically conductive object such as a metallic object. An energy delivery parameter is monitored during the delivery of energy. The value of the energy delivery parameter is compared to a predetermined magnitude threshold to determine if the value exceeds or falls below the predetermined threshold to ascertain if there is significant arcing. The energy delivery is then controlled based on the extent of the arcing observed.

It should be understood that, throughout this specification, the terms "cross" or "exceed", in various forms, are used interchangeably to refer to the value of a parameter extending beyond the threshold, including both above the threshold (for example, in the case of an "upper threshold") as well as below the threshold (for example, in the case of a "lower threshold"). The terms "cross" or "exceed" may be used in either scenario and are not intended to be limited to either above or below the threshold.

Figure 1B:
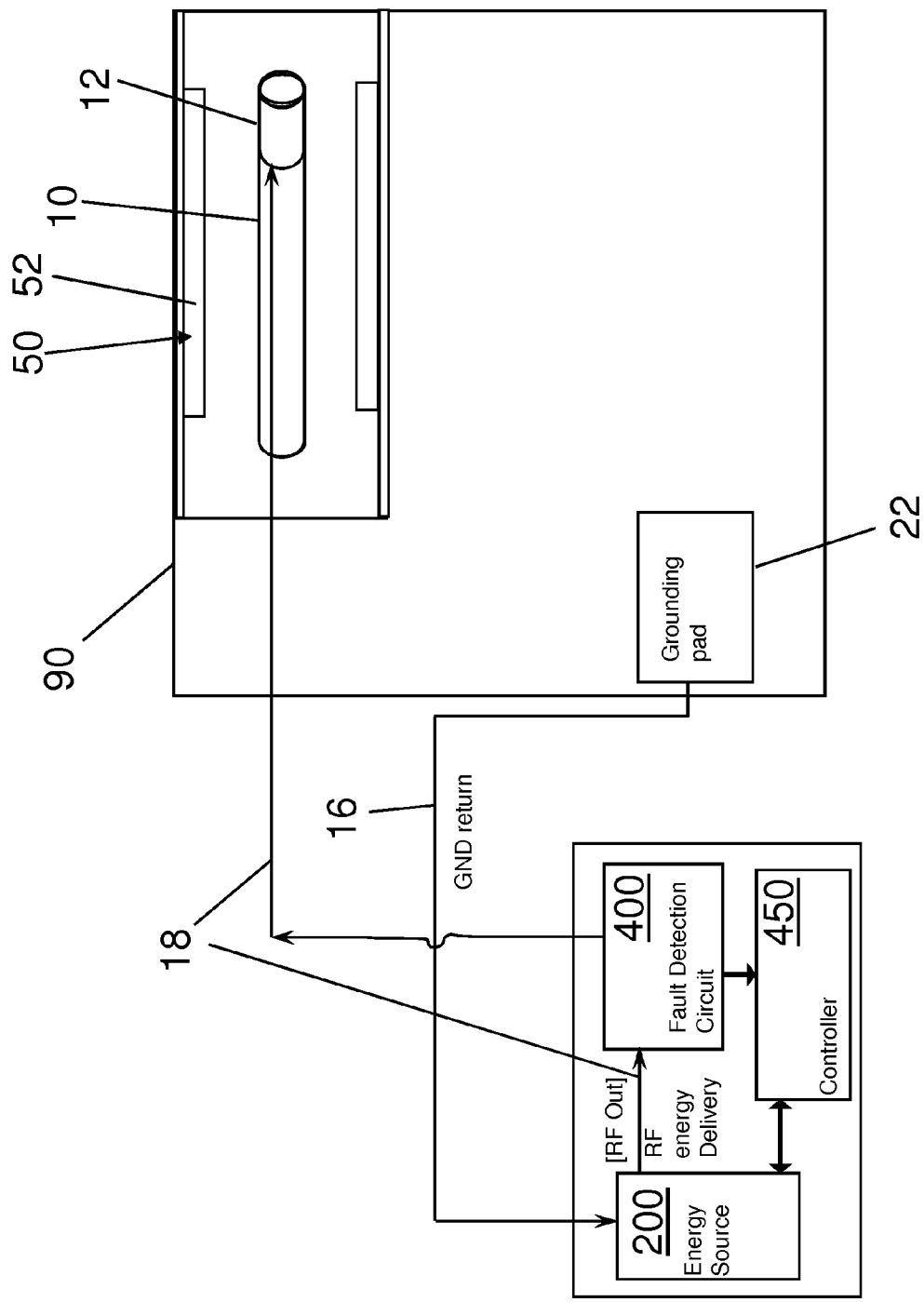
FIG. 1b is an illustration of a medical treatment system in accordance with an alternate embodiment of the present invention.

A medical treatment system, in accordance with embodiments of the present invention as shown in FIGS. 1a and 1b, comprises an energy delivery device 10 coupled to an energy source 200 to provide energy to a region of tissue within a patient's body. In one specific example, a radiofrequency (RF) energy delivery device is used in an electrosurgical application to cut or channel through a region of tissue. Energy is provided to generate an arc to enable cutting at the region of tissue. In some embodiments, as shown in FIGS. 1a and 1b, an energy delivery device 10 is used in a region of a patient's body 90 where an electrically conductive object 50, such as a metal object, is deployed or positioned. In such embodiments, the present invention allows for delivery of energy adjacent or near the electrically conductive object 50.

In one example, the electrically conductive object 50 is a stent 52 and an energy delivery portion 12 of an energy delivery device 10 may be positioned adjacent or close to the stent 52. Energy is provided by the energy delivery source 200 and through the energy delivery device 10 into the region of tissue. A change in an energy delivery parameter associated with the delivery of energy by the medical treatment system, may be observed due to the proximity of the stent 52 to the energy delivery portion 12. For example, a change in voltage, a lower impedance, an increased power output or an over-current or a current spike may be observed when there is arcing. The delivery of energy from the energy delivery device 10 may be prevented, for example by the system, if the arcing is significant and the extent of the arcing exceeds a sensitivity threshold. This may help avoid lesion formation by preventing RF energy from being transmitted through a low impedance metal object, such as stent 52. Thus, the delivery of energy from the energy delivery portion 12 of device 10 may be prevented when the energy delivery portion 12 of device 10 is positioned adjacent to or in contact with a metal object 50 such as a stent.

In one embodiment of the present invention, a fault detection circuit 400, as shown in FIGS. 1a and 1b, may be used to monitor an energy delivery parameter such as current. If the energy delivery parameter crosses a predetermined threshold, the fault detection circuit 400 detects or records an error. In the embodiments described herein, an error may mean an error and/or a fault. In a specific example, if the monitored current is 2 Amps and it exceeds a current magnitude threshold of 1 Amp, an error in the form of an over-current is detected. The extent of the faults may be determined and the controller 450 may control the output of the energy delivery device based on the extent of the faults detected and/or recorded. If the extent of the errors exceeds a sensitivity threshold before the expiry of a predetermined time period, an event or alert may be triggered and energy delivery may be controlled. For the purposes of the present specification, "expiry of a predetermined time period" can mean, for example, (i) over a specific duration of time OR (ii) by a predetermined point in time relative to, for example, the beginning of the treatment procedure or the initiation of energy delivery. In one example, the 'extent' of the errors is measured over the course of a predetermined duration or time period.

As noted above, once the extent of the errors exceeds a sensitivity threshold, an event or alert may be triggered. In some embodiments, an energy delivery and control system may provide an indication to the user and may provide the user the option of disabling the energy. For example, the energy delivery and control system may provide an error warning or other alert to the user, for example on a screen associated with the energy source. Alternatively, the delivery of energy may be automatically affected based on the extent of errors detected. For example, energy delivery may be stopped or disabled, the delivery of energy may be reduced, and/or one or more of the energy delivery parameters may be altered.

In one embodiment, the extent of the errors may be ascertained by determining the resultant magnitude of the errors detected and/or recorded. In one embodiment, if the magnitude of the detected and/or recorded errors exceeds a predetermined sensitivity threshold, energy delivery may be controlled as described herein above.

In a specific example, as outlined above, if the monitored or measured current is 2 Amps whereby it exceeds a current magnitude threshold of 1 Amp, an error in the form of an over-current is detected. In further detail, the sensitivity threshold to measure the extent of the error(s) may be predetermined to be an amount of charge proportional to a 4 Amp current. For example, if five 2 Amp over-currents are detected, then the resultant total magnitude of these over-currents (i.e. the amount of the over-currents that is above the 'current magnitude threshold' of 1 Amp, added together), is determined. If this resultant magnitude of over-currents, which in this example would be equal to about 5 Amps (i.e. five over-currents where each exceeded the threshold by 1 Amp), exceeds the sensitivity threshold (4 Amps), an event may be triggered and energy delivery may be controlled.

In another example, if one 6 Amp over-current is detected (exceeding the threshold by 5 Amps), then the resultant magnitude of this single over-current (i.e. the amount of the current that is above the 'current magnitude threshold' of 1 Amp) is determined. If this resultant magnitude (which in this example is equal to 5 Amps) exceeds the sensitivity threshold (4 Amps), energy delivery may be controlled.

In one example, the energy delivery device comprises an RF wire. As shown in FIG. 1a, current in the RF return pathway or the ground (GND) return pathway 16 from a grounding pad 22 (monopolar operation) may be coupled to the fault detection circuit 400. In another example, ground (GND) return current from the energy delivery device (bipolar operation) may be coupled to the fault detection circuit 400. Alternatively, as shown in FIG. 1b, the RF output current at the output of the energy source (i.e. along the RF energy delivery pathway 18) is coupled to the fault detection circuit 400. In some embodiments, the fault detection circuit 400 may be a component of the energy source 200. In alternate embodiments, the fault detection circuit 400 may be coupled to the energy source 200 through a controller 450. In other embodiments, the fault detection circuit may be a separate entity and may be operable to be used with any RF generator. A relay may be used to turn off or disable RF energy delivery in response to the detected fault(s).

The energy delivery parameter may be monitored continuously or intermittently. Also, the energy delivery parameter may be monitored either during the delivery of energy (i.e. concurrently with the step of delivering energy) or shortly after the step of delivering energy (i.e. energy delivery and monitoring may be performed in an alternating manner). In other words, the steps of delivering energy and monitoring may be performed either contiguously or substantially simultaneously. Furthermore, in some embodiments, the energy may be delivered continuously, intermittently or in a pulsed manner.

The monitored energy delivery parameter may be any one of, or a combination of, current, voltage, impedance or power. Alternatively, other suitable energy delivery parameters may be used and monitored. For example, if a decrease in output impedance or voltage, or an increase in output power or current, is detected by a fault detection circuit, one or more errors may be detected and/or recorded. Thus, if a value of the energy delivery parameter is not within a predetermined range or crosses or exceeds or does not meet a specified magnitude threshold, one or more errors may be detected and/or recorded. In other words, if the value of the energy delivery parameter falls below a predetermined magnitude threshold or exceeds a specified magnitude threshold (i.e. if the energy delivery parameter crosses a magnitude threshold) an error is detected.

Additionally, an extent, for example the quantity or quality, of any such detected errors may be determined or assessed. The delivery of energy may be controlled in response to the extent of errors detected. For example, the delivery of energy may be controlled if the quantity or quality of the detected exceeds a sensitivity threshold before the expiry of a predetermined time period. In some embodiments, the sensitivity threshold may be defined by a threshold number of errors, a threshold value of the energy delivery parameter or a time threshold. In alternate embodiments, the sensitivity threshold may be defined in terms of a threshold limit of an amount of charge that can be accumulated before energy delivery is controlled. In some embodiments, the sensitivity threshold may be a voltage threshold. In one particular embodiment, the sensitivity threshold may be a voltage threshold associated with the amount of charge that can be stored by a capacitor.

In some embodiments, the step of determining the extent of errors detected may comprise a step of determining the number of errors detected. In such embodiments, energy delivery may be controlled if the number of faults or errors exceeds a threshold quantity (i.e. if the amount of errors detected, regardless of the absolute value of each error, exceeds a predetermined threshold) before the expiry of a predetermined time period.

In other embodiments, the step of determining the extent of errors detected may comprise a step of determining the resultant magnitude of the one or more detected values of the energy delivery parameter. The delivery of energy from the energy delivery device may be controlled in response to the resultant magnitude of the one or more values of the energy delivery parameter. More specifically, energy delivery may be controlled if the resultant magnitude (or in other words sum) of the one or more values of the energy delivery parameter exceeds a threshold value before the expiry of a predetermined period of time. For example, the energy delivery parameter may be current, and charge from any over-currents may be stored in a capacitor. If sufficient charge is accumulated before the capacitor discharges completely, an event may be triggered and energy delivery may be controlled. In one example, the sensitivity threshold may correspond to a current value of 4 Amps which may correspond to the amount of charge that can be stored by the capacitor. If two 3 Amp over-currents (that each exceed a magnitude threshold of 1 Amp) are detected, then the capacitor may become fully charged (depending on the rate of discharge of the capacitor, fully charging the capacitor may require slightly more over-current to be detected) and the energy delivery may be controlled in response.

In still another embodiment, the step of determining the extent of errors detected may comprise a step of determining the duration of time during which the one or more errors are detected. In other words the extent of the error is determined by measuring the length of time, or duration, over which the error existed. The delivery of energy from the energy delivery device may be controlled in response to the duration of time during which the one or more faults are detected. Energy delivery may be controlled if the duration of time for the one or more faults detected exceeds a time threshold before the expiry of a predetermined period of time. In some embodiments the time threshold may be less than the predetermined period of time. In other embodiments, the time threshold may be equal to the predetermined period of time.

In some embodiments, the monitored energy delivery parameter may be current and the extent of the over-currents detected within a time period may be determined. The controller 450 may adjust the delivery of energy through the energy delivery source 200 based on the extent of the over-currents detected/recorded. As described above, in one example, the power may be shut off or the energy delivery otherwise disabled if the number of over-currents detected exceeds the sensitivity threshold before the expiry of a time period. If a large number of over-currents are detected, an event may be triggered and energy delivery may be disabled. As an illustration of this embodiment, the sensitivity threshold for the quantity of over-currents detected may be preset to about 10. If the number of over-currents detected exceeds 10 within, for example, a time period of about 300 us, an event is triggered and energy delivery may be controlled.

In some embodiments, the monitored energy delivery parameter may be impedance. One or more errors may be detected, if, for example, the impedance seen by the device falls below a threshold impedance limit. In one example, the initial value of the measured impedance may be in the range of about 200Ω. As energy is delivered via the energy delivery device, the measured impedance may rise to be in the range of about 1500Ω. Once arcing is initiated the measured impedance may drop to below about 100Ω. In one example, as the impedance drops below the threshold impedance, which may be, for example, 100Ω, one or more errors may be detected. After an arc is observed, the measured impedance may rise again to about 1500Ω. Once another arc is observed, the measured impedance may drop once again to below about 100Ω. In one example, the extent of the errors may be determined by determining the number of times the measured impedance drops below about 100Ω. Energy delivery may be controlled if the extent of errors detected is greater than the sensitivity threshold. In the aforementioned example, the sensitivity threshold may be defined as a predetermined number of errors. Energy delivery may be controlled if the number of times the impedance drops below the threshold impedance (e.g. 100Ω), before the expiry of a time period, is greater than the predetermined sensitivity threshold number. Thus, the delivery of energy from the energy delivery device may be controlled in response to the number of errors detected before the expiry of a predetermined time period.

In another example, the measured impedance may remain at or below about 100Ω for some time. In such an example, the extent of the errors may be determined by determining the duration of time over which the impedance drops below the threshold impedance. The energy delivery may be controlled if the extent of errors detected exceeds a sensitivity threshold which, in this example, may be defined as a time threshold. Thus, energy delivery may be controlled, if the duration of time during which impedance is below the threshold impedance exceeds the time threshold (before the expiry of a predetermined time period). In some embodiments, the time threshold may be equal to the predetermined time period. In other embodiments, the time threshold may be less than the predetermined time period.

In one example, the monitored energy delivery parameter may be current from the Ground Return (GND) of the energy delivery device or the output current from the energy source in the energy delivery pathway. The current may be monitored using a fault detection circuit 400 as shown in FIGS. 1a, 1b and FIGS. 2 and 3. Whenever a current spike is detected, it may constitute an error and the error can be detected and/or recorded. In other words, when the measured current crosses or exceeds a predetermined current threshold (for example, either during the positive or negative cycles of an RF waveform), an error in terms of an over-current is detected. The extent of the errors or faults in terms of over-currents may then be determined or assessed. If the extent of these over-currents exceeds a sensitivity threshold before the expiry of a predetermined time period, energy delivery may be controlled by the controller 450. In one embodiment, the extent of the over-currents may be ascertained by determining the resultant magnitude of the over-currents detected. In one embodiment, if the magnitude of the detected and/or recorded over-currents exceeds a predetermined sensitivity threshold, energy delivery may be controlled. In one example, a capacitor, such as capacitor 516a shown in FIG. 4a, may be used to determine the resultant magnitude of the detected over-currents. In other words, the amount of charge from the over-currents (that exceeds the magnitude threshold) is accumulated and stored within the capacitor. The charge may be periodically discharged by the capacitor. Thus, as charge accumulates on the capacitor some of it is discharged intermittently by the capacitor in between over-currents. Once enough charge has accumulated on the capacitor an event may be triggered and energy delivery may be controlled as described hereinabove.

In one example, the extent of the over-currents detected may involve determining the number of over-currents detected. The sensitivity threshold may be determined by a set number or quantity of over-currents that have to be detected and/or recorded before energy delivery is controlled. If the number of over-currents detected exceeds a predetermined quantity, an event can be triggered which disables energy delivery. Thus, the sensitivity threshold may be defined or adjusted such that energy delivery is not disabled until after a predetermined number of over-currents or arcs have been detected and/or recorded. This allows the physician to continue to cut and steer away after an over-current or arc is detected. The output energy stays at the nominal value required for RF cutting and as the energy delivery device 10 is moved away from the metal object it can continue to cut. Thus, the orientation or position of the energy delivery portion 12 may be re-adjusted by moving it around or away from the metal object 50, even if a few over-currents are detected while power is being delivered. This allows a user to cut close to the metal object. This further allows steerablitiy of the device around the low impedance metal object and allows a pathway to be created by cutting around or close to the metal object. In one specific example, the user may continue to cut and create a pathway in a vessel lumen, such as through an occlusion or a stenosis at the location where a stent has been deployed. The energy delivery device 10 may continue to deliver energy and cut while traversing through a stent lumen positioned within a body lumen, such as a blood vessel. Thus, depending on the setting of the sensitivity threshold, even after several over-currents, the user can steer device 10 away from the stent while continuing to deliver energy.

Figure 4A:
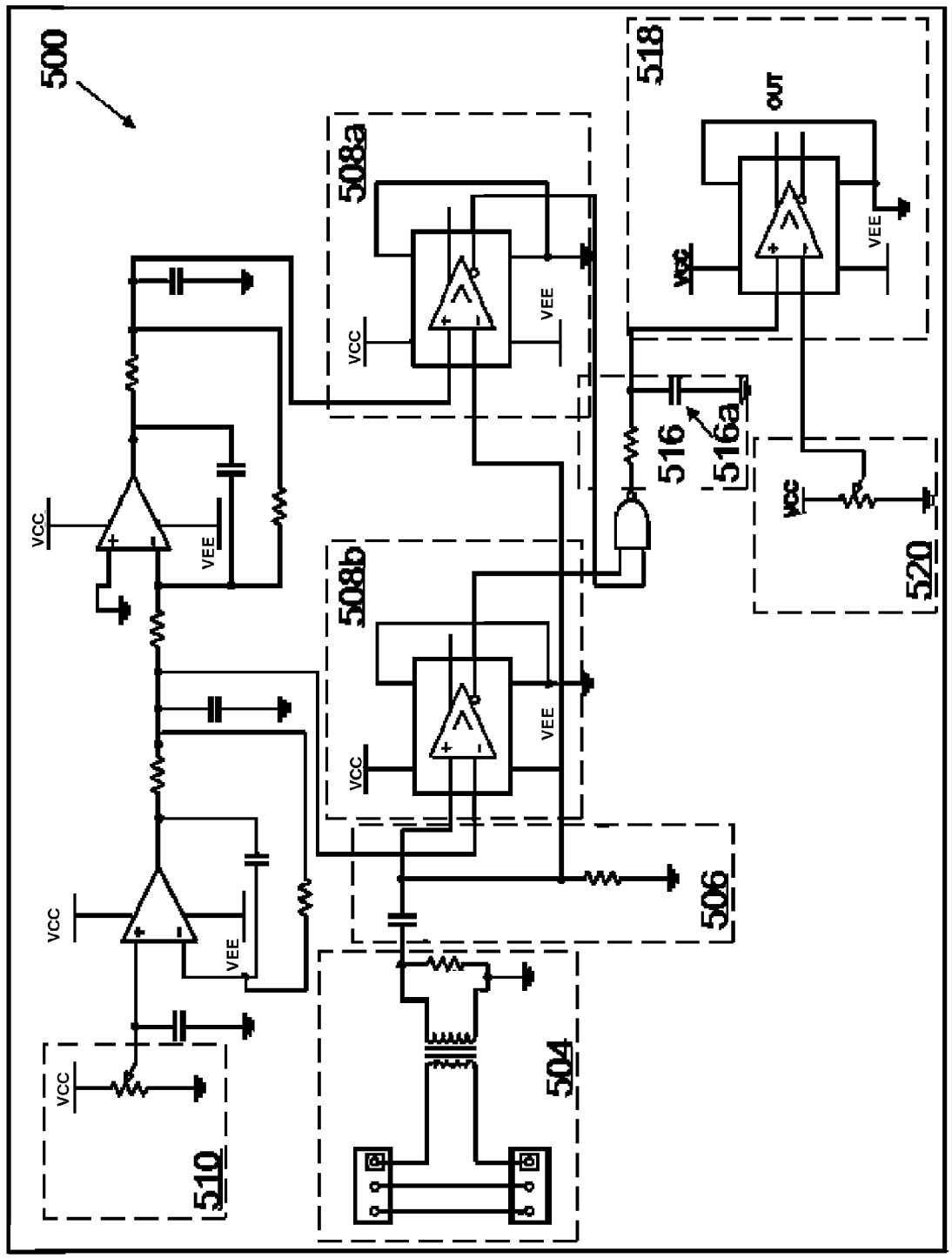
FIG. 4a illustrates a circuit diagram of a fault detection circuit in accordance with an embodiment of the present invention.
Figure 4B:
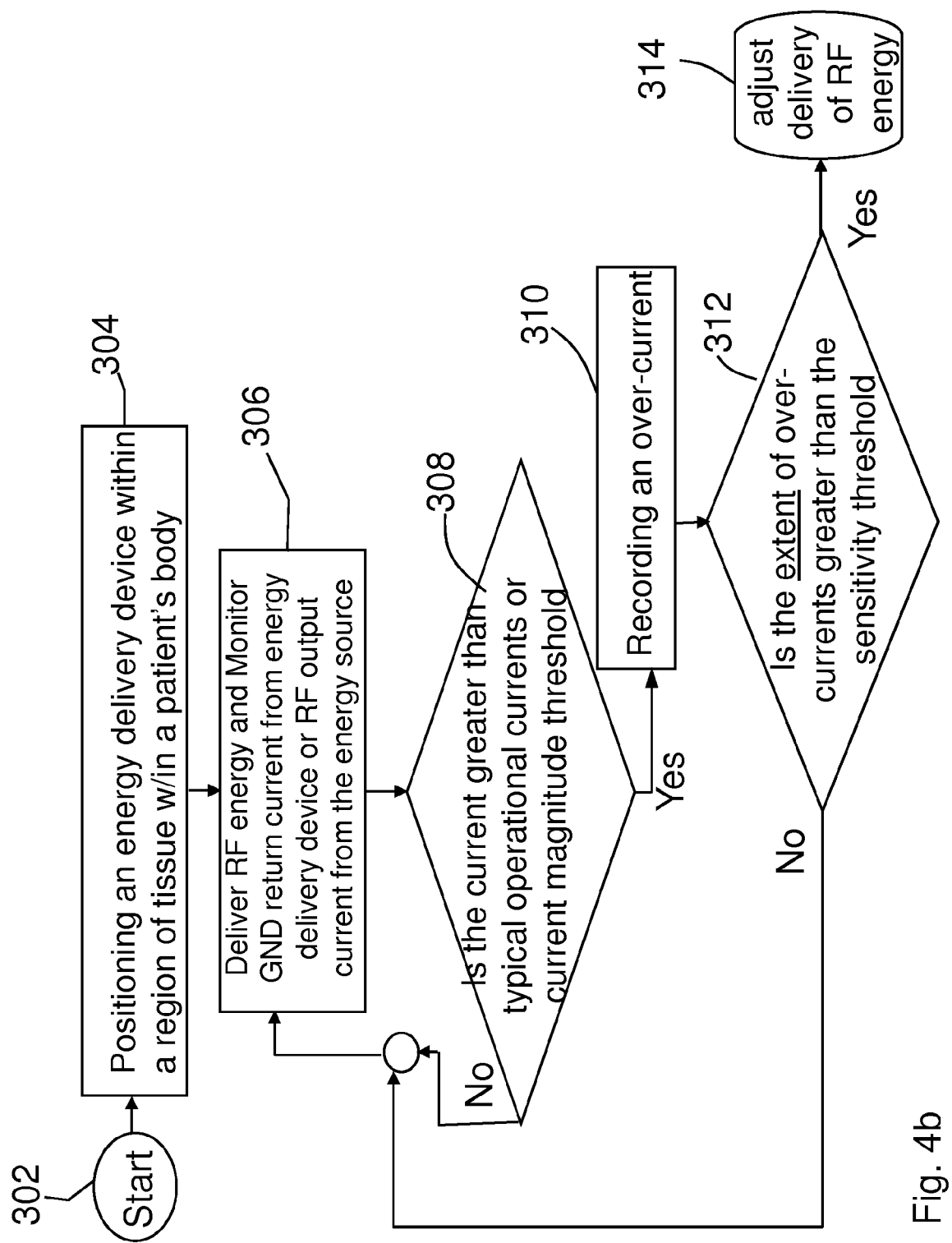
FIG. 4b is a flow chart showing a method in accordance with an embodiment of the present invention.

In accordance with one broad embodiment of the present invention, a method is disclosed for delivering energy to a region of tissue within a patient's body. FIG. 4b is a flow chart illustrating an example of such a method. As shown by step 304, an energy delivery device may be positioned within a region of tissue at a target location within a patient's body. At step 306, an RF power source may be used to supply RF energy to the energy delivery device. The energy delivery parameter that is monitored may be the current output from the ground return pathway of the energy delivery device. The measured values of the current are compared to a predetermined current range or magnitude threshold. In one example, the range of currents or current threshold may reflect normal operational currents required for cutting. In another example, the current magnitude threshold may reflect normal operational currents generated during RF ablation. The current magnitude threshold may be an adjustable threshold. In one specific example, the energy delivery device is an RF cutting device and the normal operational threshold currents are in the range of less than about 3 Amperes (Amps). In another example, the threshold current may be less than about 2 Amps. In another example, the threshold current may be less than about 1 Amp. In still another example, the threshold current may be in the range of between about 2 Amps to about 3 Amps. In another embodiment, the energy delivery device may be a radiofrequency ablation device and the normal operational current threshold may be less than about 1 Amp. In another example, the threshold current may be about 1.5 Amps.

At step 308, the measured current is analyzed to determine if it is greater than the predetermined threshold or range. If the current has peak values that exceed the current magnitude threshold or normal operational currents, at step 310 an excess current or over-current is recorded. If the monitored current is within the range of normal operational currents (below the predetermined current threshold), then the delivery of energy through the energy delivery device will not be interrupted and energy delivery can continue at step 306 and the current can continue to be monitored. At step 312, a determination is made to assess whether or not the extent of over-currents recorded within a time period is greater than the sensitivity threshold and, if it is, then the energy delivery may be adjusted at step 314. In one example, energy delivery may be stopped. In some embodiments, the extent of over-currents recorded may be determined in terms of the sum or magnitude of the over-currents recorded. In other embodiments, the extent of over-currents recorded may be determined in terms of the number or quantity of over-currents recorded. If the extent of over-currents is still below the sensitivity threshold, then at step 306 the energy delivery is continued while monitoring the current.

Referring back to FIGS. 2 and 3, a fault detection circuit 400 may be used to determine if the energy delivery portion 102 of device 100 is near or adjacent to an energy conductor such as a stent 52 or a snare during RF delivery. The fault detection circuit 400 may be used to detect, for example, currents in the ground (GND) return path of the energy delivery device 100 or currents at the RF output 18 of the energy source in the energy delivery path. If peak currents or over-currents are detected that exceed typical predetermined operational currents, an event may be triggered and energy delivery through device 100 may be stopped or otherwise affected. The fault detection circuit 400 may be integral with the RF energy delivery source 200, which may be an RF generator. In other embodiments, fault detection circuit 400 may be a separate component of the medical treatment system. In one example, the fault detection circuit 400 may receive input current from the ground return pathway 16 from a grounding pad positioned on the patient's body in a monopolar application. Alternatively, the fault detection circuit 400 may receive input current from a ground return pathway from the energy delivery device 100 in a bipolar application (not shown).

Figure 2:
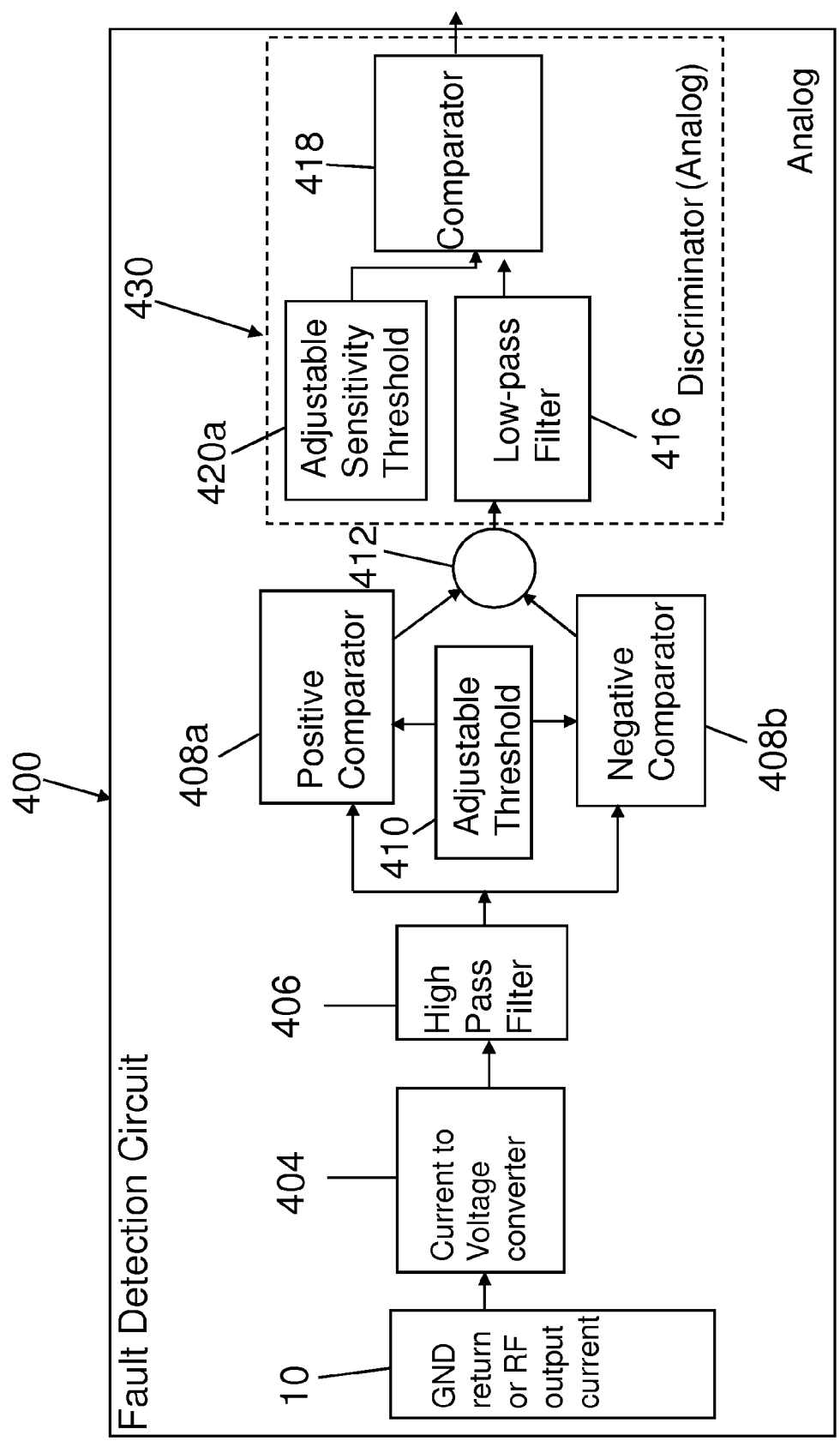
FIG. 2 illustrates a block diagram of a fault detection circuit in accordance with an embodiment of the present invention.
Figure 3:
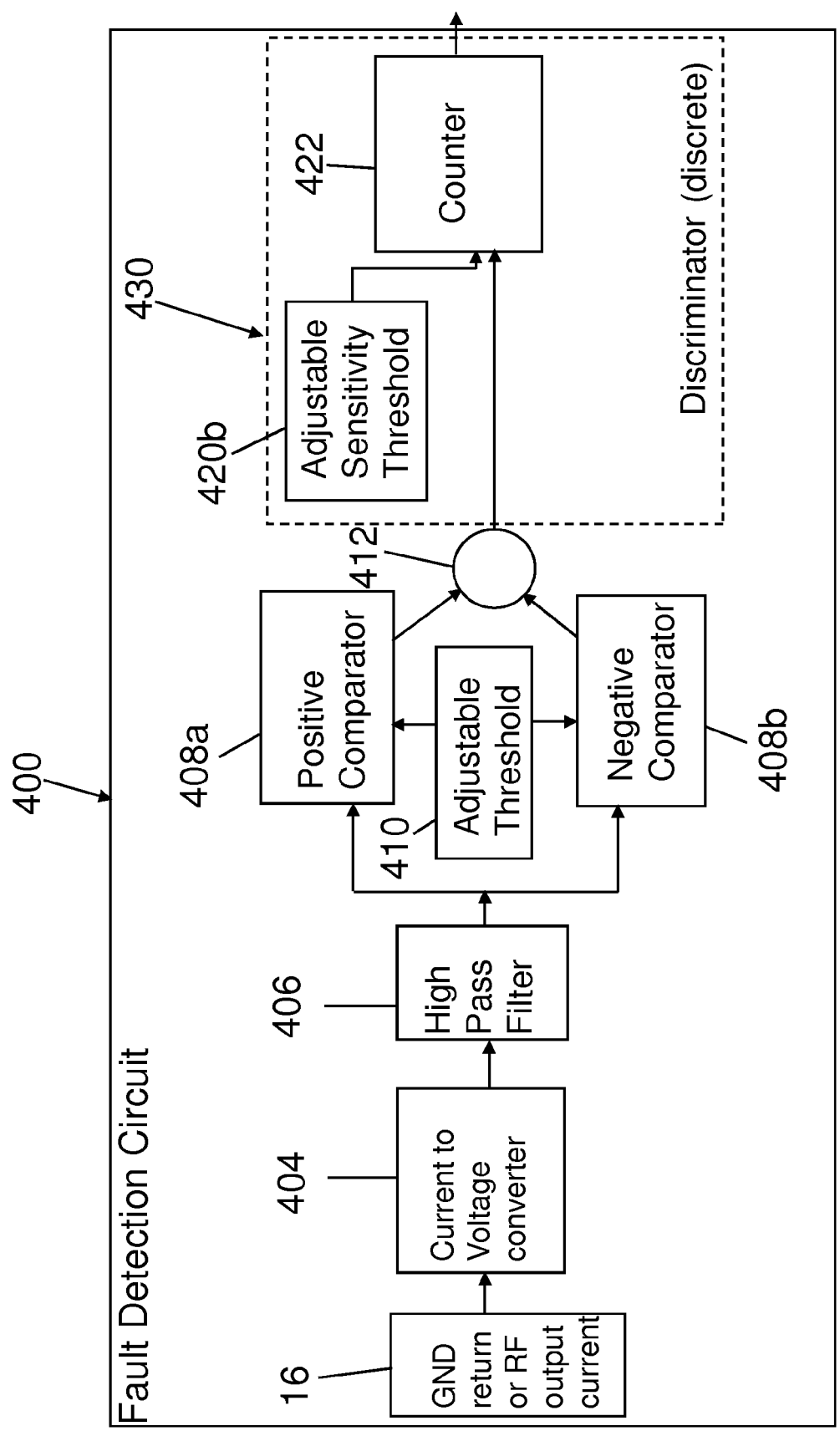
FIG. 3 illustrates a block diagram of a fault detection circuit in accordance with an alternate embodiment of the present invention.

The input current may be sensed using a current to voltage converter 404 as shown in FIGS. 2 and 3, which converts the measured current (either at RF output or GND return) of the device into voltage. In some embodiments, a voltage sense transformer may be used. In other embodiments, any current to voltage converter, for example a current sense transformer, may be used. In still other embodiments any means to sense the current may be used. In one specific example, a current sense transformer 504 is used as shown in FIG. 4a, and the output of the current sense transformer 504 may be connected to a high-pass filter 506. The high-pass filter allows for adequate rejection of the fundamental or operating frequency of the RF system. This may aid in detection of over-currents. The high-pass cut off can change based on the operational frequency. In one specific example, as shown in FIG. 4a, the high pass filter is an RC filter 506. The RC filter can be a single pole filter or a multi-pole filter. The output of filter 506 may then be routed to an input comparator 408a, which, in this example, is a positive comparator that can detect positive current peaks. An additional input comparator may be used such as a negative comparator 408b that has the ability to detect negative current peaks. In one example, comparators 508a, 508b may be used as shown in FIG. 4a.

The circuit may have an adjustable voltage threshold 410 which may be achieved through the use of a potentiometer 510 as shown in FIG. 4a. In other words the input comparators 408a, 408b may have an adjustable voltage threshold. This allows the current threshold for detecting over-currents to be adjusted as desired. In alternate embodiments the voltage threshold may be fixed. The output of the input comparators 408a, 408b may be fed into the Discriminator circuit 430. In one example, as shown in FIG. 2, the Discriminator Circuit 430 has an analog implementation which allows the magnitude of the over-current(s) to be recorded. In other words, the extent of the over-currents detected is determined in terms of the sum of the magnitude of the over-currents detected. I.e. the actual values of the currents that are above the magnitude threshold have been recorded and are added together.

As the high-frequency current peaks (over-currents) are detected by the two input comparators 408a, 408b, the over-currents are fed into, for example an OR gate 412 to create a pulse train. In the embodiment shown in FIG. 2, as noted above, the Discriminator Circuit 430 has an analog implementation. The Discriminator circuit 430 has a low pass filter 416 which presents a slowly-changing average of this pulse train to the output comparator 418 of the Discriminator circuit 430. If the pulses are frequent enough, the voltage at the input of comparator 418 will rise above the sensitivity threshold and will trip the Discriminator Circuit output.

The low pass filter 416 may help reduce the risk of false positives in terms of false over-currents being detected. In one example, the low pass filter 416 may be an RC filter 516 at the input of the comparator. The RC filter 516 allows the charge from the detected over-currents to be stored within capacitor 516a. The charge from an over-current or cumulative charge from multiple over currents is stored by the capacitor 516a within the RC time constant of the capacitor. In one example, the RC time constant of the capacitor is about 100 μs. The voltage at the capacitor 516a node is fed as an input of the output comparator 518. When the voltage at the capacitor 516a node is equal to or greater than the sensitivity threshold voltage input to the output comparator 518, this determines that the extent (i.e. in this embodiment, the sum, or in other words, the resultant magnitude) of the detected over-currents exceeds the sensitivity threshold.

In one example, the sensitivity threshold may be fixed. In another example, the output comparator 418 may have an adjustable sensitivity threshold 420a. In one example a potentiometer 520 may be used to adjust the sensitivity threshold by changing the voltage at the input of the output comparator 418. This changes the voltage to which the capacitor 516a must charge and proportionately the length of time required for the charge to accumulate on the capacitor 516a. If the potentiometer is set to a higher voltage, than a greater number of over-currents may occur before the controller allows the power supply to the energy delivery device to be shut off, thereby disabling energy delivery. In one example, the sensitivity threshold may be set to allow 10×1 Amp current peaks or over-currents to be detected within a 100 μs time period prior to disabling the energy delivery. Alternatively, or in addition, the sensitivity threshold may allow 5×2 Amp current peaks or over-currents to be detected. In another embodiment, the sensitivity threshold may be set to allow, for example, 10×3 Amp current peaks to be detected within a 100 μs time frame. Other examples are possible as well.

The output of the comparator may then be conveyed to a controller, which controls the delivery of energy through the energy delivery device. In one embodiment, the controller may prevent the delivery of energy through the energy delivery device based on the sum or magnitude of over-currents detected. In other words the controller may shut-off the power delivery based on the extent of over-currents detected.

With reference now to FIG. 3, an alternate embodiment is shown in which the Discriminator Circuit 430 comprises a discrete or digital implementation. The number of current peaks may be detected and, rather than a low-pass filter and comparator, a digital counter 422 may be used. The digital counter 422 may have an external reset. In one example, if the number of over-currents detected before the counter is reset exceeds a digital threshold, the energy delivery may be disabled. The sensitivity threshold in the digital implementation of the Discriminator circuit 430 is the digital threshold, which represents the number of pulses or over-currents that should be detected before the output of the Discriminator Circuitry 430 is asserted and conveyed to the controller. The controller may then control the delivery of energy through the energy delivery source based on the number of over-currents detected. In one example, the digital sensitivity threshold 418b may be variable, or may be adjustable by the user. In this example, the number of over-currents that must be detected by the counter 422 before an output is asserted, can be changed as desired by the user. In another embodiment, the sensitivity threshold may be fixed and the number of over-currents that must be detected by the counter 422 may thus be fixed as well.

Figure 5A:
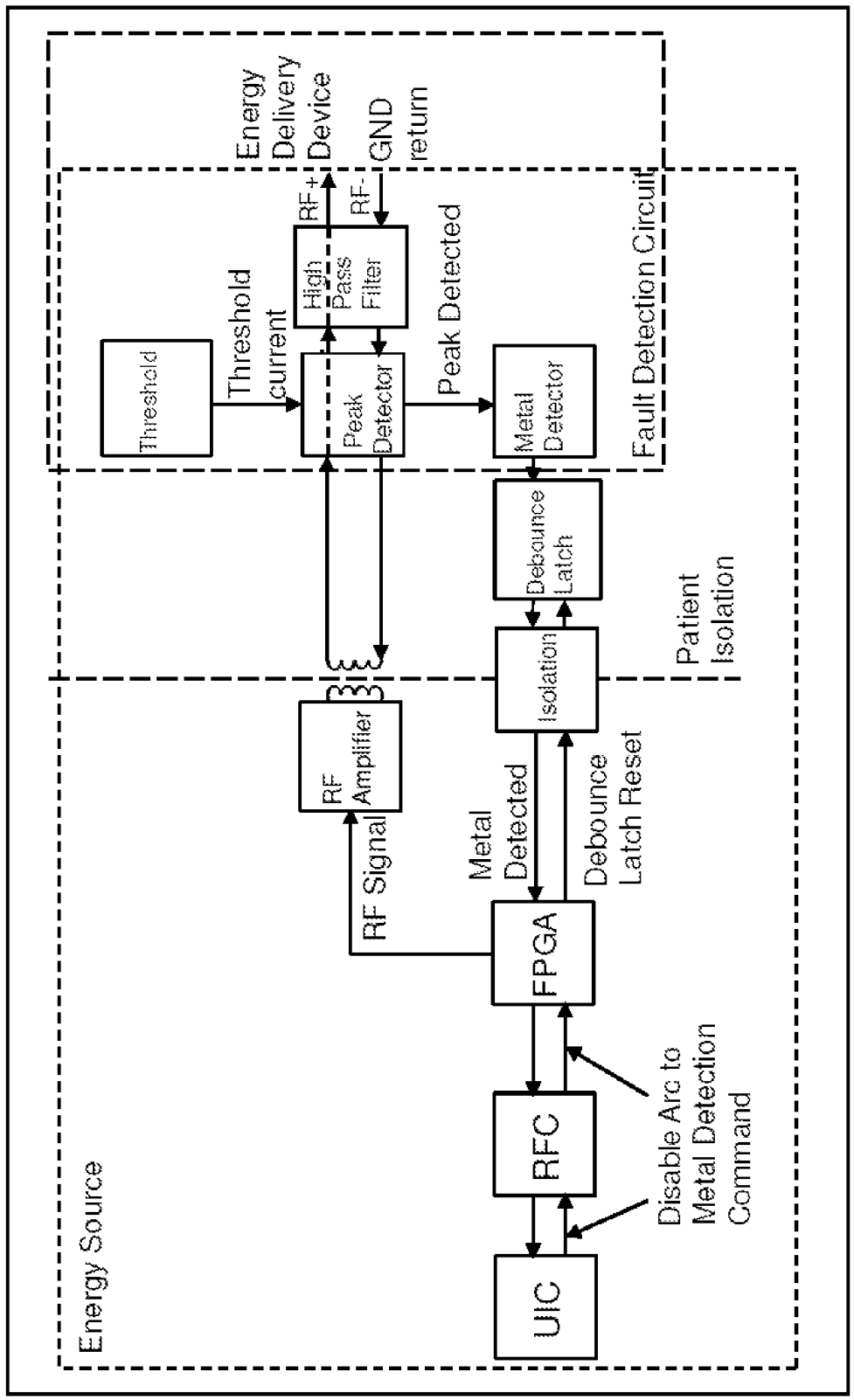
FIG. 5a illustrates a block diagram of an energy delivery system in accordance with an embodiment of the present invention.
Figure 5B:
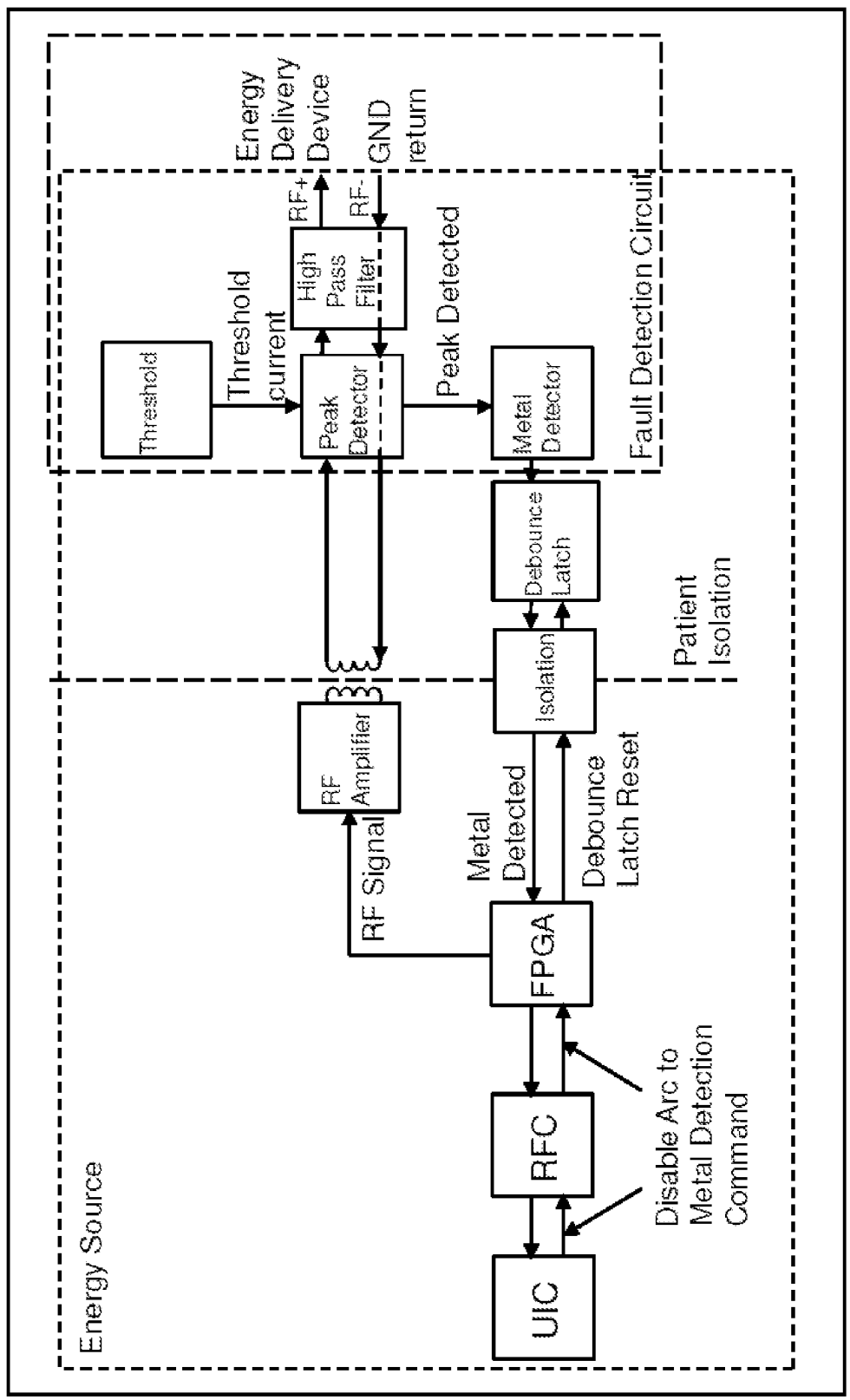
FIG. 5b illustrates a block diagram of an energy delivery system in accordance with an alternate embodiment of the present invention.

With reference now to FIGS. 5a and 5b, block diagrams of a medical treatment system in accordance with embodiments of the present invention are shown. An energy delivery source is shown which includes a fault detection circuit. In some embodiments the fault detection circuit may be a separate component of the medical treatment system. In one example, the fault detection circuit receives input from the ground return as indicated by "RF−", in FIG. 5a. In another example, the fault detection circuit receives input from the RF Amplifier of the energy delivery source, as shown in FIG. 5b.

The RF Amplifier of the energy delivery source of the generator provides input current to the energy delivery device shown as "RF+". The RF amplifier is coupled to an FPGA (field programmable gate array) which may be coupled to an RF board Controller (RFC) and a User Interface Controller (UIC) which help control the output to the energy delivery device. The Control circuitry, which includes the RFC, the UIC and the FPGA, receives feedback from the fault detection circuit and can control the delivery of energy from the energy delivery source based on the input received from the fault detection circuit. Once the Discriminator Circuit (not shown) of the fault detection circuit determines that the extent of the over-currents (magnitude or sum of over-currents) exceeds a sensitivity threshold, the output generated by the Fault Detection Circuit may be conveyed to a latch and its output may be set to high. This output may then be conveyed to the Control Circuit, which allows the energy delivery from the energy delivery source to be controlled based on the output of the Fault Detection Circuit. Thus the delivery of RF signal from the RF amplifier may be stopped. The latch output may then be reset. In some examples, the latched signal is detected via serial read or interrupt. (The Peak Detector and High Pass Filter of the Fault Detection Circuit do not impede flow of RF current, but rather monitor it). The medical treatment system may also include a feature allowing a user to disable the arc-to-metal-detection function.

With further reference to FIGS. 5a and 5b, the current from the output of the energy delivery device is received as input into the current to voltage converter and high pass filter. In a specific example, the high pass filter is a 1.5 MHz nominal −3 db point single-pole high pass filter. Furthermore, in one specific example, the Peak Detector activates for current spikes of either polarity that exceed 40 ns in duration at a threshold current value of 1.7 A. In other words the Peak Detector detects an error/fault if the current exceeds 1.7 A for a duration of at least about 40 ns. The energy delivery is then controlled if the extent of errors or faults detected exceeds a sensitivity threshold. The sensitivity threshold may be defined or set based on one or more of the magnitude (in terms of the amplitude) as well as the pulse width of the pulse train of current to be detected. In one embodiment, the sensitivity threshold is set as a time threshold or duration of about 300 μs±30 μs. In an example of this, if pulses (that are at or above a threshold amplitude of 1.7 Amps having a pulse width of about 113 ns) are observed for a duration of at least about 300 μs±30 μs, energy delivery may be controlled. More specifically, once the Peak detector has been supplied with a continuous string of pulses for duration equal to or exceeding the sensitivity threshold of about 300 μs±30 μs, the Metal Detector within the Fault detection circuitry is activated.

In another example, the sensitivity threshold is set as a time threshold or duration of about 30 μs±3 μs. If pulses (that are at or above the threshold amplitude of 1.7 Amps having a pulse width of about 500 ns) are observed for a period of time greater than or equal to about 30 μs±3 μs, the energy delivery may be controlled. Thus, once the Peak detector has been supplied with a continuous string of pulses (having a pulse width of at least about 500 ns) for duration equal to or exceeding a sensitivity threshold of about 300 μs±3 μs, the Metal Detector is activated. The output generated by the Fault Detection Circuit may then be conveyed to the Control circuitry to modify the output of the energy delivery device.

As mentioned above, the Control circuitry which includes the RFC, the UIC and the FPGA receives feedback from the fault detection circuit and can control the delivery of energy from the energy delivery source based on the input received from the fault detection circuit.

In alternate embodiments, the energy delivery device may be used near an electrically conductive object 50 that is a bare metal snare. In still another example, the electrically conductive object 50 may be an RF wire. In further examples, the electrically conductive object 50 may be any metal object positioned within a patient's body such as a metal screw. In one example, the electrically conductive object 50 may be a metal RF wire or a snare that may be used as a target for positioning the energy delivery device. In some embodiments, the electrically conductive object 50 may be another electrosurgical device. In one specific example, the electrically conductive device 50 may be a stent-graft and the medical treatment system may be used to create a fenestration through a stent-graft through the delivery of RF energy. In other words, the RF energy delivery device may be used to induce graft perforation of a stent-graft as discussed in U.S. patent application Ser. No. 11/905,448, filed on Oct. 1, 2007, previously incorporated herein by reference in its entirety. In one example, the stent-graft may be positioned in a renal artery. In another example, the stent-graft may be positioned in a branch of the aorta. In one specific example, the medical treatment system may be used to create a fenestration through a stent-graft positioned in the thoracic aorta.

In various alternatives, the energy delivery device 10 may have an electrically conductive energy delivery portion 12 along at least along a portion of the energy delivery device. The energy delivery portion 12 is coupled to the energy source 200 such that the energy delivery source 200 provides RF energy to the energy delivery portion 12. The energy delivery portion 12 may comprise one or more active electrodes positioned on a portion of the energy delivery device 10. In one embodiment, the energy delivery device is an RF energy delivery device that comprises at least one active electrode. In other embodiments, more than one active electrode may be positioned on the energy delivery device.

In some embodiments of the present invention as disclosed above, the energy source may provide energy in the range of between about 100 KHz to about 1.5 MHz. In one example the energy source is provided in the form of an RF generator that is capable of delivering energy in the frequency range of between about 400 KHz to about 550 KHz, more specifically, between about 450 KHz to about 480 KHz. In one example, energy is delivered at a frequency of about 460 KHz. The energy delivery device may be used to provide energy for a range of applications within a patient's body. This may include use in cardiac applications, for treatment within a patient's vasculature.

In some embodiments, power may be provided at greater than about 30 Watts. In some embodiments, the power may be supplied at greater than about 50 Watts. The voltage supplied may be greater than 200 Vrms. In some embodiments the energy delivery device may be an RF cutting device. In some such embodiments, the voltage is supplied in the range of between about 200 Vrms to about 300 Vrms. In some embodiments, the voltage may be supplied in the range of between about 200 Vrms and 400 Vrms. In other embodiments, the supplied voltage is greater than or equal to about 400 Vrms.

In an alternate embodiment, the energy delivery device may be an RF ablation device with an active ablation electrode. In some embodiments, the voltage supplied may be greater than about 50 Vrms. The power may be supplied in the range of between about 2 Watts and about 8 Watts. In some such embodiments, the Voltage may be between about 100 Vrms to about 200 Vrms.

Thus, as described herein, in accordance with various embodiments, a method is disclosed for delivering energy within a region of tissue within a patient's body. The method helps avoid significant arcing while allowing use of an energy delivery device in the vicinity of an electrically conductive object such as a metallic object. An energy delivery parameter is monitored during the delivery of energy. The value of the energy delivery parameter is compared to a predetermined magnitude threshold to determine if the value exceeds or falls below the predetermined threshold to ascertain if there is significant arcing. The energy delivery is then controlled based on the extent of the arcing observed.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of delivering energy to a region of tissue within a patient's body using a medical treatment system, said medical treatment system comprising an energy delivery device coupled to an energy source, the method comprising the steps of:
    delivering energy through said energy delivery device;
    monitoring an energy delivery parameter associated with the delivery of energy by the medical treatment system;
    detecting one or more errors if one or more values of the energy delivery parameter exceed a predetermined magnitude threshold;
    determining or assessing an extent of the errors detected over a predetermined period of time; and
    controlling the delivery of energy if the extent of the errors detected exceeds a sensitivity threshold over the predetermined period of time.

2. The method of claim 1, wherein the step of determining the extent of errors detected comprises determining a number of errors detected.

3. The method of claim 1, wherein the step of determining the extent of errors detected comprises determining an overall magnitude of the one or more values of the energy delivery parameter that exceed the predetermined magnitude threshold.

4. The method of claim 1, wherein the energy delivery parameter is selected from the group consisting of: current, voltage, impedance and power.

5. The method of claim 1, wherein the energy delivery device is a radiofrequency cutting device.

6. The method of claim 1, wherein the energy delivery device is a radiofrequency ablation device.

* * * * *